(12) United States Patent
Nielsen et al.

(10) Patent No.: US 8,419,637 B2
(45) Date of Patent: Apr. 16, 2013

(54) SIZING AND POSITIONING TECHNOLOGY FOR AN IN-THE-EAR MULTI-MEASUREMENT SENSOR TO ENABLE NIBP CALCULATION

(75) Inventors: Larry Nielsen, Burlington, MA (US); Christopher J. Poux, Mercerville, NJ (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 903 days.

(21) Appl. No.: 11/995,006

(22) PCT Filed: Jun. 13, 2006

(86) PCT No.: PCT/IB2006/051892
§ 371 (c)(1),
(2), (4) Date: Nov. 11, 2008

(87) PCT Pub. No.: WO2007/004083
PCT Pub. Date: Jan. 11, 2007

(65) Prior Publication Data
US 2009/0069645 A1    Mar. 12, 2009

Related U.S. Application Data

(60) Provisional application No. 60/695,725, filed on Jun. 30, 2005.

(51) Int. Cl.
*A61B 5/00* (2006.01)

(52) U.S. Cl.
USPC .......................................................... 600/301

(58) Field of Classification Search .................. 600/301
See application file for complete search history.

(56) References Cited

U.S. PATENT DOCUMENTS

| | | |
|---|---|---|
| 4,601,294 A | 7/1986 | Danby et al. |
| 5,213,099 A | 5/1993 | Tripp |
| 5,673,692 A | 10/1997 | Schulze et al. |
| 5,743,261 A | 4/1998 | Mainiero et al. |
| 5,853,005 A | 12/1998 | Scanlon |
| 6,004,274 A | 12/1999 | Nolan et al. |
| 6,115,621 A | 9/2000 | Chin |
| 6,172,743 B1 | 1/2001 | Kley et al. |
| 6,253,871 B1 | 7/2001 | Aceti |
| 6,283,915 B1 | 9/2001 | Aceti et al. |
| 6,454,718 B1 | 9/2002 | Clift |
| 6,556,852 B1 | 4/2003 | Schulze et al. |
| 6,694,180 B1 | 2/2004 | Boesen |
| 6,773,405 B2 | 8/2004 | Fraden et al. |
| 6,850,789 B2 | 2/2005 | Schweitzer et al. |
| 2001/0027335 A1 | 10/2001 | Meyerson et al. |
| 2003/0092975 A1 | 5/2003 | Casscells et al. |
| 2004/0064054 A1 | 4/2004 | Clift |
| 2004/0078219 A1 | 4/2004 | Kaylor et al. |
| 2004/0258263 A1 | 12/2004 | Saxton et al. |
| 2005/0049471 A1 | 3/2005 | Aceti |
| 2005/0059870 A1 | 3/2005 | Aceti |

FOREIGN PATENT DOCUMENTS

| | | |
|---|---|---|
| EP | 0770349 A1 | 5/1997 |
| EP | 1495783 A1 | 1/2005 |
| EP | 1671578 A1 | 6/2006 |
| JP | 04256727 A | 9/1992 |
| JP | 2003290152 A | 10/2003 |
| WO | 03001180 A2 | 1/2003 |
| WO | 2005034742 A1 | 4/2005 |

*Primary Examiner* — Jerry Lin

(57) ABSTRACT

An in-the-ear (ITE) physiological measurement device (2) includes a structure (4) formed for easy insertion into multiple shaped and sized ear canals. An inflatable balloon (6) surrounds an end portion of the structure (4) to be positioned in the ear. Optionally, a mushroom shaped tip (22) is connected with an end of the structure (4) and carries a plurality of sensors (8). Inflation of the balloon (6) expands the tip (22) radially to position the sensors (8) proximate to vascular tissue within the ear canal. Once suitably positioned, the one or more sensors (8) sense physiological signals from the vascular tissue and bone structure.

24 Claims, 4 Drawing Sheets

SIZING AND POSITIONING TECHNOLOGY FOR AN IN-THE-EAR MULTI-MEASUREMENT SENSOR TO ENABLE NIBP CALCULATION

CROSS REFERENCE TO RELATED APPLICATIONS

This application claims the benefit of U.S. provisional application Ser. No. 60/695,725 filed Jun. 30, 2005, which is incorporated herein by reference.

BACKGROUND

The following relates to monitoring physiology. It finds particular application to an in-the-ear structure that is inserted in the ear canal to suitably position one or more physiological sensors within the inner ear to capture information indicative of physiological phenomena including blood pressure, respiration, perfusion index, blood oxygen, pulse rate, and body temperature, for example.

Physiological signals have been measured from within the ear. However, there are no multi-parameter physiological measurement devices that non-invasively measure blood pressure from within the ear. Examples of barriers that frustrate such development include the varying size and shape of the human ear canal from person to person, an inability to strategically position sensors within the ear canal to optimally receive physiological signals, and an inability to protect sensing devices from contamination through contact with inner ear tissue while measuring physiological signals.

In one aspect, an in-the-ear physiological measurement device includes a structure formed for insertion into an ear canal. One or more sensors are operatively coupled to a portion of the structure that is positioned in the ear. An inflatable balloon is operatively coupled to the portion of the structure positioned in the ear and inflates to position the one or more sensors proximate to tissue within the ear canal. Once suitably positioned, the one or more sensors sense physiological signals from the surrounding tissue and bone structure.

One advantage includes measuring physiological signals from within the ear.

Another advantage resides in non-invasively measuring blood pressure from within the ear.

Another advantage is continuously measuring non-invasive blood pressure from with the ear.

Another advantage resides in an in-the-ear device that forms to different shaped and sized ear canals.

Another advantage is positioning the sensor within the ear canal to optimally receive physiological signals therefrom.

Another advantage is positioning the sensor within the ear canal with ideal force and pressure to ensure close coupling of sensors with tissue without causing blanching of the tissue.

Another advantage is positioning the sensor within a well perfused physiological site even if the body is experiencing peripheral shutdown due to shock or other conditions.

Another advantage is the prevention of over insertion into the ear.

Another advantage is measuring physiological signals through a sheath that mitigates contamination of the physiological sensors.

Another advantage resides in an in-the-ear physiological signal measuring device that equalizes ear pressure with ambient pressure, especially during balloon inflation and deflation.

Still further advantages will become apparent to those of ordinary skill in the art upon reading and understanding the detailed description of the preferred embodiments.

Figure 1:
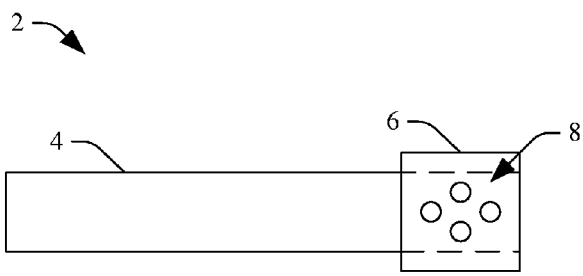
FIG. 1 illustrates an in-the-ear physiological measurement apparatus for measuring physiological signals from within an ear.

FIG. 1 illustrates an in-the-ear (ITE) physiological measurement apparatus 2 (hereafter "the ITE apparatus 2") for measuring one or more physiological signals (e.g., blood pressure, pulse, blood oxygen, perfusion, temperature, respiration . . . ) from within an ear canal. The ITE apparatus 2 includes a structure 4 that inserts into the ear canal. The structure 4 is dimensioned to enter the ear canal to a suitable depth and adapts to various shaped ear canals (e.g., different curvatures). That is, the structure 4 is small in diameter compared to the diameter of the ear canal. In a preferred embodiment, the structure 4 projects into the ear canal such that an end portion is positioned proximate to a bony region of the ear or other relatively quiet zone of the ear canal.

The end portion of the structure 4 residing in the ear canal includes an annular inflatable balloon 6. The inflatable balloon 6 surrounds the end portion of the structure 4 (as illustrated) or suitable portions thereof. The inflatable balloon 6 ideally supports one or more sensors 8 that are operatively coupled to a surface of the balloon 6 and that measure physiological signals. Suitable sensors include light emitting diodes (LEDs), an infrared (IR) source, light detectors, a pressure transducer, a microphone, and a thermistor, for example. The sensors 8 are strategically positioned on the balloon 6. For example, a light detecting sensor typically is positioned to minimize or prevent absorption of light not indicative of the physiological process under measurement (e.g., light from outside the ear, light emitted from another sensor located on the balloon 6 . . . ). Although depicted as circular in FIG. 1, the one or more sensors 8 can be any shape. Alternatively, the sensors could be mounted within the end portion of the structure 4 and could be moved into contact with the tissue once inserted into the ear.

The inflatable balloon 6 is inflated to position the one or more sensors 8 proximate to appropriate tissue within the ear canal with ideal force and pressure to ensure close coupling of sensors with tissue but without causing decreased perfusion or blanching of the tissue. For adult humans, this includes inflating the balloon 6 to conform to the widely varying ear canal diameters from about 6 mm to about 13 mm. For neonates and small pediatrics, where the ear canal diameter various from about 4 mm in diameter to about 7 mm in diameter, smaller and shorter ITE devices are used. Typically, sensors for measuring blood oxygen are positioned proximate to ear canal tissue that is perfused with arterial blood supplied by branches of the External as well as the Internal Carotid Arteries, thus serving as a well perfused physiological site even if the body is experiencing peripheral shutdown due to shock or other conditions. Such sensors include an energy emitting means (e.g., an LED, an IR source . . . ) and an energy detecting means that detects energy transmission through the vascular tissue. In another example, a temperature sensor (e.g., a thermistor) is also positioned proximate to vascular tissue. In yet another example, sensors for sensing audio signals (e.g., a microphone) indicative of pulse pressure sounds, and/or respirations are suitably positioned in relatively quite regions of the ear canal to mitigate sensing extraneous audio signals (noise).

The inflatable balloon 6 is also used to facilitate non-invasively measuring blood pressure. For a non-invasive blood pressure measurement, the inflatable balloon 6 is inflated until it occludes blood flow in a portion of the ear proximate a blood pressure sensor(s) (e.g., a pressure transducer) operatively connected to the inflatable balloon 6. The pressure in the inflatable balloon 6 is then suitably released to deflate the inflatable balloon 6. A systolic and a diastolic blood pressure are obtained during inflation and/or deflation using an auscultatory approach (e.g., via a microphone operatively connected to the balloon 6) and/or an oscillometric approach (e.g., via optical sensing components attached to the balloon).

A continuous non-invasive blood pressure is measured by obtaining an initial blood pressure measure as describe above and then re-inflating the balloon 6 to a mean pressure. A servo mechanism periodically adjusts balloon pressure to locate a maximum pulse waveform amplitude indicative of mean blood pressure. As long as the derived mean pressure is relatively close to the initial pressure and/or the pulse waveform amplitudes are relatively close, the derived continuous systolic, diastolic, and mean blood pressure are calculated with high accuracy.

Figure 2:
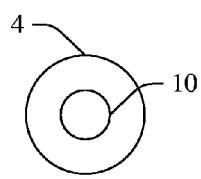
FIG. 2 illustrates an in-the-ear physiological measurement apparatus with a single channel for housing sensor wiring and inflating/deflating an inflatable balloon to position sensors proximate to inner ear tissue.
Figure 3:
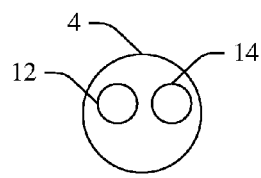
FIG. 3 illustrates an in-the-ear physiological measurement apparatus with separate channels for housing sensor wiring and inflating/deflating an inflatable balloon.
Figure 4:
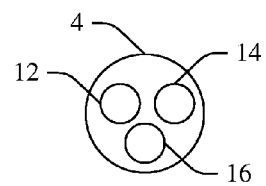
FIG. 4 illustrates an in-the-ear physiological measurement apparatus with an air passage channel for equalizing air pressure between the ear and the environment when inflating and deflating the balloon.

The structure 4 includes one or more passageways (as illustrated in FIGS. 2-4 infra) that extend through the structure 4. Such passageways house sensor data, power, and control wires, provide a hermetically sealed channel for inflating/deflating the balloon 6, and/or allow pressure inside the ear to equalize with the environment during balloon inflation/deflation. FIG. 2 depicts an aspect in which the structure 4 includes a channel 10 for both housing sensor wiring and inflating/deflating the balloon 6. The channel 10 isolates the wires from the inner ear environment, mitigating contamination of both the ear and the sensor wiring and provides a pressurized air conduit to the balloon 6. FIG. 3 depicts an aspect in which the structure 4 includes separate channels for sensor wiring and inflating/deflating the balloon 6; one or more first channels 12 house sensor wiring and a second channel 14 provides the pressurized air conduit for inflating/deflating the balloon 6. FIG. 4 depicts an aspect in which an optional channel 16 provides an ear pressure stabilizing mechanism that allows ear pressure to equalize with the environment during balloon inflation and/or deflation. The channel 16 mitigates pressure build-up in the ear during balloon inflation and/or deflation and potential pain therefrom. The examples in FIG. 2-4 depict the structure 4 and the passageways 10-16 with circular shaped cross-sections. These particular shapes are not limitative and are provided for explanatory purposes. It is to be understood that the structure 4 and/or the passageways 10-16 can be essentially any shape (e.g., oval, rectangular, irregular . . . ) conducive to the ear canal.

Figure 5:
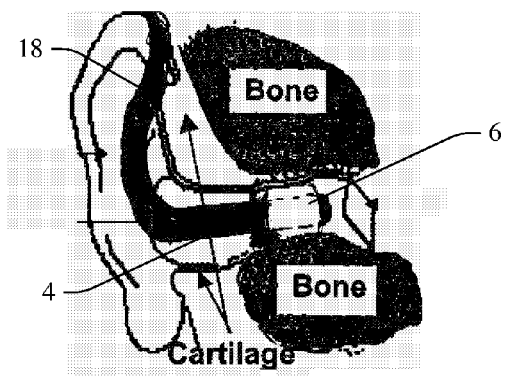
FIG. 5 illustrates an in-the-ear physiological measurement apparatus positioned within an ear.

FIG. 5 illustrates the ITE apparatus 2 inserted into an ear canal. The structure 4 is inserted such that the end portion with the balloon 6 residing in the ear canal is in a bony region of the ear. The balloon 6 is inflated to position the sensors 8 proximate to inner ear tissue to sense signals indicative of physiological states, including blood pressure, temperature, pulse, respiration, and blood oxygen, for example.

Figure 6:
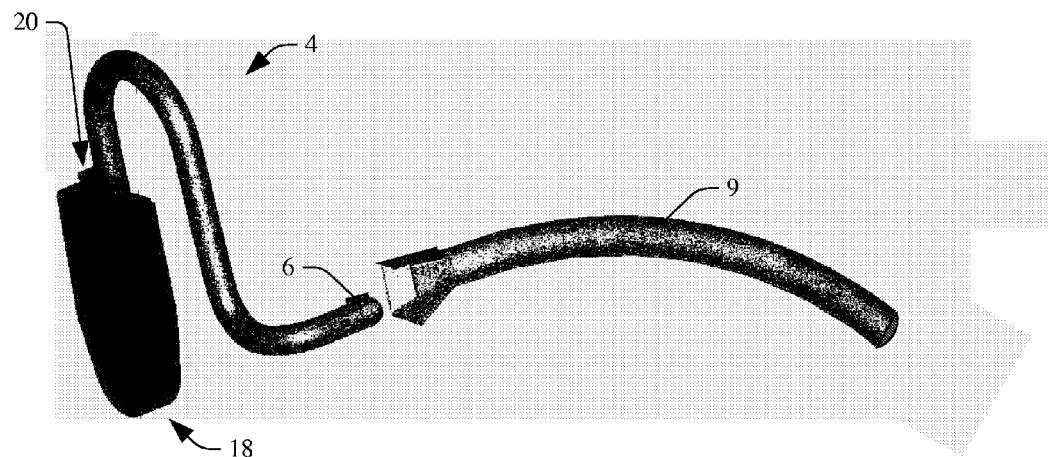
FIG. 6 illustrates a connection point between an in-the-ear physiological measurement apparatus, a supporting behind-the-ear device, and a protective sheath that mitigates contamination of the physiological sensors.

FIG. 6 illustrates the ITE apparatus 2 with an optional sheath 9 placed over the structure 4 and balloon 6 to protect the ear and the structure/balloon/sensor assembly from contamination. In one aspect, the sheath can be semi-permeable to allow air flow, but prevent fluid from moving from one side of the sheath to the other side. In another aspect, the sheath prevents substantially all matter from moving from one side of the sheath to the other side. The structure/balloon/sensor assembly can be disposable, washable, and/or sterilizable.

The structure 4 is shown supported in the ear by a (BTE) ear piece 18. The structure 4 can be operatively attached to the ear piece 18. Such attachment can be through a fastening means including a threaded connector, a snap, a set screw, an adhesive, a rivet, etc. FIG. 6 shows an exemplary connection region 20 between the structure 4 and the optional ear piece 18. A protective sheath 9 may be used to mitigate contamination of the physiological sensors if desired. In another aspect, the structure 4 and the ear piece 18 can be formed as a single unit.

Figure 7:
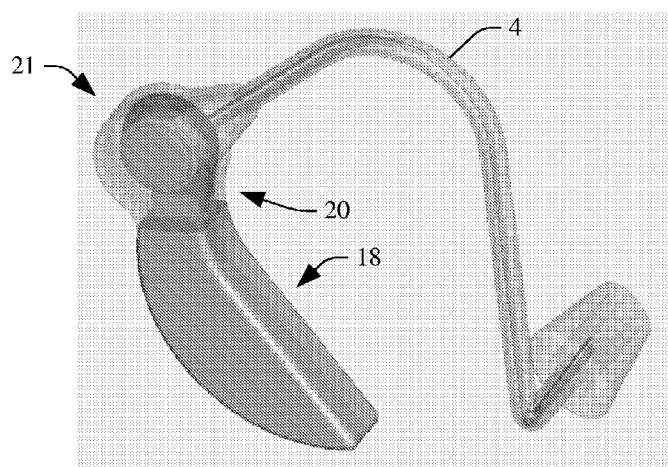
FIG. 7 illustrates an in-the-ear physiological measurement apparatus connected to a behind-the-ear supporting device.

FIG. 7 shows the BTE device 18 connected to the ITE device 2. The ITE device 2 includes a battery 21 which powers both devices. With this embodiment, the ITE device 2 and battery 21 are low cost and disposable.

FIGS. 5-7 above illustrate the optional ear piece 18 as a behind-the-ear supporting device. In a preferred embodiment, the ITE apparatus is connected to a behind-the-ear (BTE) device (18) by means of a semi-rigid connector tube that is formed to fit over and/or around the ear to prevent over insertion and to hold in position the ITE device with optimised orientation and positioning. It is to be understood that other types of supporting devices are contemplated. For example, the structure 4 can be mounted to supporting devices that attach to a region of the head, neck, shoulders, etc.

The BTE device 18 can house various electronics that receive physiological signals from the sensors 8 (e.g., via sensor wire extending through the passageways 10 and 12 briefly described above) and transmit the physiological signals to another transceiver (not shown) worn by the subject (e.g., a transceiver worn around the neck or waist) or to a remote device (not shown) such as a monitoring device, a database, a computer, and a graphical display. The BTE device 18 can optionally include a processor (not shown), memory (not shown), and a battery (not shown). The processor is used to control the sensors and electronics, process raw data, and read data from the sensors; the memory is used to store data and/or configuration; and the battery powers the processor, active sensors, and the transceiver.

Figure 8:
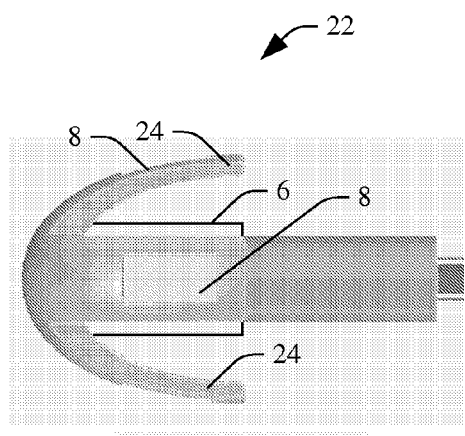
FIGS. 8-12 illustrate various views of a suitable tip for holding sensors associated with an in-the-ear physiological measurement apparatus.
Figure 9:
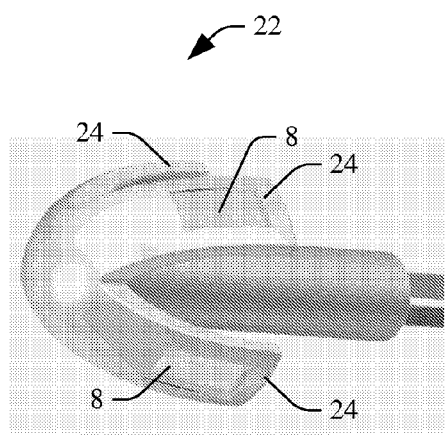
Figure 10:
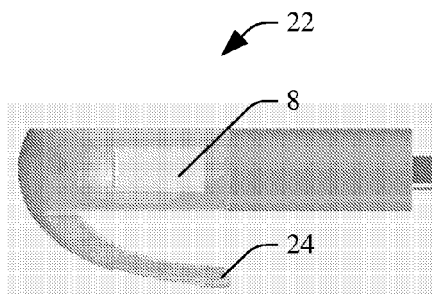
Figure 11:
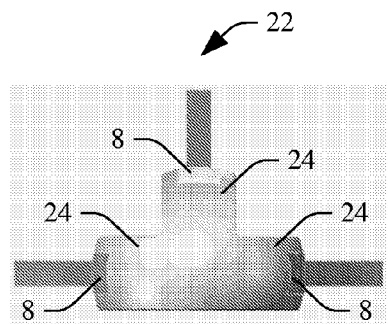

In the embodiment of FIGS. 8-11, the one or more sensors 8 are located on a soft, pliable tip 22 (rather than directly on the inflatable balloon 6, or on the ITE device tip on a side opposite the inflatable balloon 6) that is operatively connected to the end of the structure 4 inserted into the ear. The balloon 6 is shown in FIG. 8, but has been removed from the FIGS. 9-11 for clarity of illustration. Upon inserting the structure 4 in the ear, the sensors 8 are still positioned by inflating the balloon 6; however, inflating the balloon 6 expands sensor carrying leaves 24 of the tip 22, which positions the sensors 8 proximate to inner ear tissue.

Figure 12:
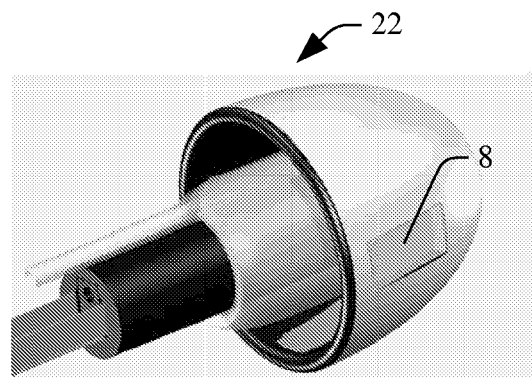
Figure 13:
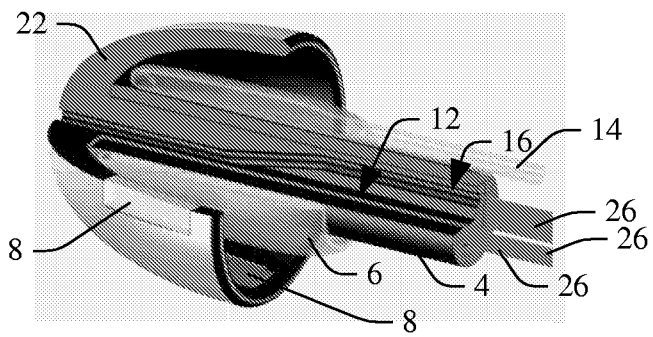
FIG. 13 is a perspective view in partial section illustrating an uninflated balloon for insertion into the ear canal.
Figure 14:
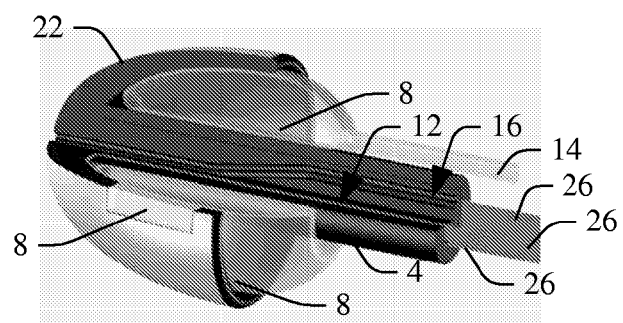
FIG. 14 is a perspective view in partial section illustrating an inflated balloon.

FIG. 12-14 depict the tip 22 as an expandable mushroom shaped element. In this embodiment, inflating the balloon 6 from the insertion level of FIG. 13 expands the soft, pliable tip 22, which positions the sensors 8 proximate to inner ear tissue (See FIG. 14). The tip 22 and/or balloon 6 also serve as an optical reflector, helping to reflect light from a light emitter through the tissue, from the bone, through the tissue, reflectively and transmissively, to the reflector, from the reflector back through the tissue and so forth, until it finally reaches the light detector. The back side of the tip 22 is opaque which blocks unwanted ambient light coming from within the ear canal. The tip (22) and/or the balloon (6) also serves as buffer between external ambient airflow and thermistor (8) that is measuring a surrogate of core body temperature. Flex-circuit connectors 26 each extend through the structure 4, bend around the balloon 6, and flexibly interconnect with an associated sensor 8.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An in-the-ear (ITE) physiological measurement device including:
   a structure formed for insertion into an ear canal;
   a tip operatively connected to a region of the structure inserted in the ear;
   one or more sensors operatively connected to the tip that is inserted in the ear; and
   an inflatable balloon operatively coupled to the portion of the structure inserted in the ear, the inflatable balloon inflates to position the one or more sensors proximate to tissue within the ear canal such that the one or more sensors non-invasively sense signals from the surrounding tissue and bone structure indicative of at least blood pressure.

2. The ITE physiological measurement device according to claim 1, wherein the structure is inserted to position the one or more sensors proximate to at least one of a bony region and a quite zone of the ear canal.

3. The ITE physiological measurement device according to claim 1, wherein the inflated balloon positions the one or more sensors located on the tip proximate to the vascular tissue with ideal force and pressure to ensure close coupling of sensors with tissue without causing decreased perfusion or blanching of the tissue.

4. The ITE physiological measurement device according to claim 1, the tip and/or the balloon serves as a reflector to reflect and direct sensor sourced light through the tissue of the ear, reflectively and transmissively, into a light detector while blocking ambient light such that the sensor further senses signals indicative of at least a blood oxygen level.

5. The ITE physiological measurement device according to claim 1, the tip and/or the balloon serves as buffer between external ambient airflow and a thermistor that measures a surrogate of core body temperature.

6. The ITE physiological measurement device according to claim 1, wherein the balloon is disposed between the structure and the tip to inflate and expand the tip as the balloon is inflated in order to position the one or more sensors located thereon proximate to the vascular tissue.

7. The ITE physiological measurement device according to claim 1, wherein the one or more sensors include one or more of: a light emitting diode, an IR source, a light detector, a thermistor, a pressure transducer, and a microphone.

8. The ITE physiological measurement device according to claim 1, wherein the inflatable balloon expands to position the one or more sensors within an adult ear canal from about 6 mm in diameter to about 13 mm in diameter, and within a pediatric ear canal from about 4 mm in diameter to about 7 mm in diameter.

9. The ITE physiological measurement device according to claim 1, further including an electronic device which:
   causes the balloon to inflate until blood flow in the proximate tissue in the ear is occluded;
   causes the balloon to deflate; and
   determines a systolic blood pressure and a diastolic blood pressure from the sensor signals.

10. An in-the-ear (ITE) physiological measurement device comprising:
    a structure formed for insertion into an ear canal, the structure including a passageway that extends through the structure for equalizing ear pressure within the ear canal with ambient air pressure;
    one or more sensors operatively coupled to a portion of the structure that is inserted in the ear; and
    an inflatable balloon operatively coupled to the portion of the structure inserted in the ear, the inflatable balloon inflates to position the one or more sensors proximate to tissue within the ear canal such that the one or more sensors non-invasively sense signals from the surrounding tissue and bone structure indicative of at least blood pressure.

11. The ITE physiological measurement device according to claim 10, wherein the one or more sensors are operatively attached to the inflatable balloon.

12. The ITE physiological measurement device according to claim 10, the structure including:
    an air passageway that extends through the structure to the balloon for inflating and deflating the balloon; and
    a wire passageway that extends through the structure to the one or more sensors for housing sensor wires for carrying power or control signals to the sensors and data from the sensors.

13. The ITE physiological measurement device according to claim 10, further including:
    a semi-rigid connector tube that is formed to fit over and/or around the ear to prevent over insertion of the structure to hold the structure in position with optimized orientation and positioning.

14. An in-the-ear (ITE) physiological measurement device including:
    a structure formed for insertion into an ear canal;
    one or more sensors operatively coupled to a portion of the structure that is inserted in the ear;
    an inflatable balloon operatively coupled to the portion of the structure inserted in the ear, the inflatable balloon inflates to position the one or more sensors proximate to tissue within the ear canal such that the one or more sensors non-invasively sense signals from the surrounding tissue and bone structure indicative of at least blood pressure; and
    a sheath that protects the structure, the balloon, the one or more sensors, and the ear canal from cross contamination.

15. The ITE physiological measurement device according to claim 14, wherein the structure is inserted to position the one or more sensors proximate to surrounding deep ear canal tissue which is perfused with arterial blood supplied by branches of at least one of External and Internal Carotid Arteries and serves as a well perfused physiological site even if the body is experiencing peripheral shutdown due to shock or other conditions.

16. The ITE physiological measurement device according to claim 14, further including:
a battery that powers one or more components.

17. A method for measuring blood pressure within the ear canal, comprising:
inserting an in-the-ear structure into an ear canal to a desired depth;
inflating the inflatable balloon operatively connected to an end portion of the in-the-ear structure to occlude blood flow in the ear tissue proximate to the inflatable balloon and to position one or more sensors proximate to vascular tissue of the ear canal; and
using the one or more sensors to obtain a systolic and a diastolic blood pressure signals from the surrounding tissue and bone structure while inflating and/or deflating the inflatable balloon.

18. The method according to claim 17, further including measuring blood pressure through one or more of an auscultatory approach and an oscillometric approach.

19. A method for continuously measuring blood within the ear canal, comprising:
inserting an in-the-ear structure into an ear canal to a desired depth;
inflating an inflatable balloon operatively connected to an end portion of the in-the-ear structure to position one or more sensors proximate to vascular tissue of the ear canal;
obtaining at least one of an initial systolic and diastolic blood pressure measure reading with the one or more sensors;
determining a mean blood pressure measurement from the reading;
inflating the balloon within the ear canal to the mean blood pressure;
periodically adjusting balloon pressure; and
capturing a maximum pulse waveform amplitude indicative of the mean blood pressure using the one or more sensors.

20. The method according to claim 19, further including deriving at least one of a systolic and a diastolic blood pressure from at least one of the mean blood pressure and one or more pulse waveform amplitudes.

21. A physiological measurement device for measuring physiological signals from within the ear canal, comprising:
a first structure formed for easy insertion into multiple shaped and sized ear canals;
a second structure that supports the first structure to facilitate maintaining the position of the first structure within the ear canal;
an inflatable balloon disposed around a portion of the first structure to be positioned in the ear, the inflatable balloon expands radially with inflation;
a radially expanding tip connect with the first structure and extending at least partially around the inflatable balloon such that inflation of the balloon radially expands the tip; and
a sensor carried by the tip to the pressed into sensing interaction within an ear canal.

22. The physiological measurement device according to claim 21, the sensor senses one or more of blood pressure, continuous blood pressure, pulse, blood oxygen level, perfusion, body temperature, and respiration.

23. The physiological measurement device according to claim 21, wherein the one or more sensors include one or more of the following: a light emitting diode, an IR source, a light detector, a thermistor, a pressure transducer, and a microphone.

24. The physiological measurement device according to claim 21, wherein the physiological measurement device is operatively connected to the secondary device by a semi-rigid connector tube that is formed to fit over and/or around the ear to prevent over insertion and to hold the physiological measurement device in position with optimised orientation and positioning.

* * * * *